US 7,727,476 B2

(12) United States Patent
Ingenhoven et al.

(10) Patent No.: US 7,727,476 B2
(45) Date of Patent: Jun. 1, 2010

(54) DEVICE FOR ASPIRATING AND DISPENSING LIQUID SAMPLES

(75) Inventors: Nikolaus Ingenhoven, Uerikon (CH); Noa Schmid, Wuppenau (CH); Stefano Fornito, Bertschikon (CH)

(73) Assignee: Tecan Trading AG, Mannedorf (CH)

( * ) Notice: Subject to any disclaimer, the term of this patent is extended or adjusted under 35 U.S.C. 154(b) by 1183 days.

(21) Appl. No.: 11/056,696

(22) Filed: Feb. 11, 2005

(65) Prior Publication Data

US 2005/0244303 A1    Nov. 3, 2005

Related U.S. Application Data

(63) Continuation-in-part of application No. 09/993,252, filed on Nov. 19, 2001, now Pat. No. 6,869,571.

(30) Foreign Application Priority Data

Nov. 17, 2000  (CH) .................................... 2252/00
Nov. 29, 2000  (CH) .................................... 2314/00

(51) Int. Cl.
*B01L 3/02*    (2006.01)
(52) U.S. Cl. ..................... 422/100; 436/49; 436/54; 436/180; 73/864.17
(58) Field of Classification Search .............. 436/49, 436/54, 180; 422/100; 73/864.01–864.25
See application file for complete search history.

(56) References Cited

U.S. PATENT DOCUMENTS 3,911,749 A * 10/1975 Hendry ..................... 73/864.22
4,231,990 A * 11/1980 Jottier ....................... 422/100

* cited by examiner

*Primary Examiner*—Jan M Ludlow
(74) *Attorney, Agent, or Firm*—Notaro, Michalos & Zaccaria P.C.

(57) ABSTRACT

A device for aspirating and dispensing liquid samples comprising a pump that comprises a cylindrical chamber, a piston movable in this cylindrical chamber, and a piston drive that engages the piston. The device further comprises a tip connected to the cylindrical chamber with a line, and a channel system that discharges into the cylindrical chamber for flushing or rinsing the latter. The device is characterized in that the piston entirely seals this cylindrical chamber from the channel system, if the piston is positioned in the cylindrical chamber in such a way that a free piston end comes to rest between the channel system and the line. Preferably, the cylindrical chamber is located in a cylinder block, which comprises two parts that are separated by and enclosing an intermediate channel system. The channel system most preferably is implemented as a coherent cavity. According to a first embodiment, the cylindrical chamber is implemented as a sleeve that is inserted in a boring located in a cylinder block. According to a second embodiment, the cylindrical chamber is implemented as a boring located in a cylinder block. Furthermore, the invention also concerns systems with, for example, 384 or more such devices that are arranged in an array.

14 Claims, 3 Drawing Sheets

DEVICE FOR ASPIRATING AND DISPENSING LIQUID SAMPLES

RELATED PATENT APPLICATIONS

This is a Continuation in Part Application of the regular U.S. patent application Ser. No. 09/993,252 filed on Nov. 19, 2001 granted as U.S. Pat. No. 6,869,571 which claims priority of the Swiss Patent Application No. CH 2000 2252/00, filed Nov. 17, 2000 and the Swiss Patent Application No. CH 2000 2314/00, filed Nov. 29, 2000.

FIELD OF THE INVENTION

The invention concerns a device for aspirating and dispensing liquid samples according to the preamble of independent claim 1, as well as systems which include multiple devices of this type.

BACKGROUND OF THE INVENTION

It is known that droplets with a volume of more than 10 µl can be dispensed from the air very easily, since if the pipette is correctly manipulated, the droplets leave the pipette tip of their own accord. The droplet size is then determined by the physical properties of the sample liquid, such as surface tension or viscosity. The droplet size thus limits the resolution of the quantity of liquid to be dispensed.

The aspirating and dispensing, i.e. the pipetting of liquid samples with a volume of less than 10 µl, in contrast, typically requires instruments and techniques which guarantee the dispensing of such small samples. The dispensing of a liquid with a pipette tip, i.e. with the endpiece of a device for aspirating and/or dispensing sample liquid, can occur from the air ("from air") or by touching a surface. This surface can be the solid surface of a container ("on tip touch"), into which the liquid sample is to be dispensed. It can also be the surface of a liquid in this container ("on liquid surface"). A mixing procedure following the dispensing is recommended—particularly for very small sample volumes in the nanoliter or even picoliter range—so that uniform distribution of the sample volume in a diluent is ensured.

Disposable tips significantly reduce the danger of unintentional transfer of parts of the sample (contamination). Simple disposable tips are known (so-called "air-displacement tips"), whose geometry and material is optimized for the exact aspirating and dispensing of very small volumes. The use of so-called "positive-displacement tips", which have a pump plunger inside, is also known.

For automation of the pipetting process, two procedures must be differentiated from one another: the defined aspiration and the subsequent dispensing of liquid samples. Between these procedures, typically the pipette tip is moved by the experimenter or by a robot, so that the aspiration location of a liquid sample is different from its dispensing location. For the precision of aspiration and dispensing, only the liquid system is essential, which includes a pump (e.g. a diluter implemented as a syringe pump), tubing, and an endpiece (pipette tip). Among the many possible pumps for highly precise aspirating and dispensing of liquids, commercially available devices with the name "CAVRO XL 3000 Modular Digital Pump" or "CAVRO XP3000 plus Modular Digital Pump", sold by the firm Tecan Systems Inc., 2450 Zanker Road, San Jose, Calif. 95131 USA (formerly Cavro Scientific Instruments Inc., Sunnyvale, Calif., USA), have, for example, proven themselves. Such pumps include a cylinder with a piston movable therein and a stepping motor for driving the piston. The stepping motor operates at a voltage of 24 V and is controlled by an external computer or microprocessor. Further details can, for example, be found in the "Operators Manual P/N 724043C" from Cavro Scientific Instruments Inc.

A device and a corresponding method are known from U.S. Pat. No. 5,763,278. They involve automatic pipetting of small volumes, with the device including a pipetting needle, a diluter with a liquid outlet having a syringe, and a valve. The syringe includes a piston and a piston drive. A line connects the needle and the liquid outlet of the diluter, with the diluter and the line containing an essentially incompressible liquid. A pulse generator is located in the device and connected with the incompressible liquid in the line so that mechanical pulses with a force of at least 0.01 Ns can be output directly into the liquid of the line. A pulse of this type serves for driving the liquid out of the needle. The droplet size is defined by a targeted advance of the diluter piston and the droplet is ejected from the needle with a pulse. By defining the volume with the diluter, the droplet size and its reproducibility depends on the resolution of the diluter and is limited by it. Another pipetting device of this class which includes a piston pump and a pulse generator in the form of a piezoelectric element is known from JP 09 327628.

Multichannel systems in which 4, 8, or 12 pipetting channels are distributed on one line have been known for some time. The tips are either arranged in a fixed raster (e.g. the MiniPrep device series from the firm CAVRO Scientific Instruments Inc., Sunnyvale, Calif., USA) or they can be spread out along one line (e.g. the GENESIS device series from TECAN Schweiz AG, Seestrasse 103, CH-8708 Männedorf). The pipetting channels are either operated jointly via a stepping motor with one or more syringes or individually operated via the same number of diluters as syringes.

Multichannel systems for volumes in the sub-microliter range are known in the form of fixed two-dimensional combs (e.g. the PixSys4500 from Cartesian Technologies, Inc., 17851 Sky Park Circle, Irvine, Calif. 92614, USA) or from EP 0 956 449. These two-dimensional combs of pipettes, however, are typically no longer sufficient for the current demands for sample throughput.

Multichannel pipettors arranged in three dimensions are also known. They can be implemented as 96 tip devices with 96 individual hoses and 96 individual syringes, which are each driven in groups of 8 by a joint stepping motor (e.g. the MICROLAB MPH-96 Workstation from Hamilton Bonaduz AG, P.O. Box 26, 7402 Bonaduz, Switzerland). This system is very costly due to the large number of syringes and motors. In addition, it is difficult to remove interfering air bubbles from all of the hoses.

Arrays with up to 384 individual glass syringes with cannulas have also been arranged in the raster of a 384 microplate. The plungers of the syringes are moved simultaneously by one single stepping motor (e.g. the Hydra from Robbins Scientific, 1250 Elko Drive, Sunnyvale, Calif. 94089-2213, USA). The method is costly due to the many syringes. It cannot be expanded for disposable tips.

In place of diluters, syringes, and pistons, metal bellows are also used (cf. U.S. Pat. No. 5,638,986). Due to the smaller mass to be moved, dispensing speeds are achieved which are suitable for dispensing volumes down to 0.5 µl from the air (e.g. the Liliput Dispenser from Fluilogic Systems Oy, Luoteisrinne 4, 02270 Espoo, Finland). A disadvantage is, however, that the metal bellows cannot be calibrated like, for example, a diluter.

The most frequent constructional principle of three-dimensionally arranged multichannel pipettors comprises a plate to which and/or in which the 96 or 384 pistons or plungers are attached. As known from U.S. Pat. No. 4,087,248, this plate is moved, with the pistons for aspirating and/or dispensing, up and down by one or more motors. In U.S. Pat. No. 4,087,248 (see there FIG. 3), feeding reagents, solutions, and the like, to the tips of syringes is described: According to one embodiment, the syringes are in fluid connection with a reservoir through orifices. When the plunger is moved above the orifices, fluid from the reservoir will enter the syringe. This fluid may then be expelled from the syringe into the tips by moving the plunger downwardly. In an alternative embodiment, a so-called "Eppendorf Syringe", comprising a hollow plunger with a central post, is employed. The central post is spring mounted and connected to a foot. An O-ring is compressed between the foot and a projection which is rigidly attached to the plunger. The foot is shaped to leave a gap between the foot and the inner wall of the syringe. The O-ring provides a seal with the inner wall of the syringe. By pressing on the central post, the foot is lowered with respect to the projection and O-ring so as to provide fluid connection between the hollow center of the plunger and the syringe. Fluid can therefore dispensed by means of the plunger or withdrawn from the syringe employing suction. On the one hand, the alternative embodiment with the "Eppendorf Syringes" appears to be too complex in particular for a multichannel pipetter with 96 or more pipetting channels. On the other hand, the first embodiment suffers from the fact that the plunger has to be moved against the pressure of the rinsing or flushing liquid for aspiration of a liquid sample; the same pressure acting with the plunger for dispensing liquid samples. Such pressure differences provoke a complex drive and monitoring system, if accurate pipetting is targeted.

SUMMARY OF THE INVENTION

An object of the present invention is to suggest an alternative device for aspirating and dispensing liquid samples this device comprising one or a multiplicity of pipetting or dispensing channels and means for removal of interfering air bubbles from all of the channels and pipette tips. It is also an object of the present invention that the aspiration and dispense movement of the piston is not impaired by any pressurized flushing or rinsing liquid. It is a further object of the present invention that the pipette tips can be flushed or rinsed without moving liquid with the plunger. These and further objects are achieved with the features of the claims. In particular, this invention provides a device for aspirating and dispensing liquid samples comprising a pump that comprises a cylindrical chamber, a piston movable in this cylindrical chamber, and a piston drive that engages the piston. The device according to the present invention further comprises a tip connected to the cylindrical chamber with a line, and a channel system that discharges into the cylindrical chamber for flushing or rinsing the latter, wherein the piston entirely seals this cylindrical chamber from the channel system, if the piston is positioned in the cylindrical chamber in such a way that a free piston end comes to rest between the channel system and the line. Preferred embodiments and additional inventive features derive from the dependent claims.

BRIEF DESCRIPTION OF THE DRAWINGS

The present invention will now be described in more detail with reference to schematic drawings, which illustrate preferred exemplary embodiments and are not to restrict the extent of the present invention.

DETAILED DESCRIPTION OF THE INVENTION

Figure 1:
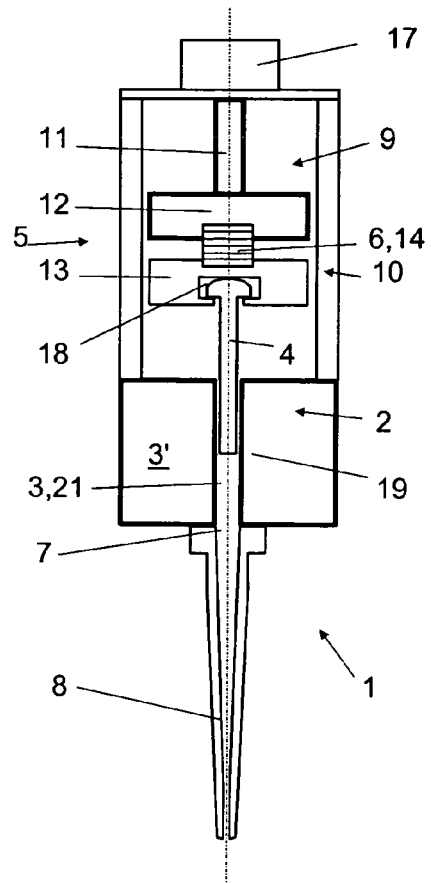
FIG. 1 shows a vertical section through a simple device for aspirating and dispensing liquid samples.

FIG. 1 shows a device 1 for aspirating and dispensing liquid samples having a pump 2. This pump comprises a cylindrical chamber 3, which in turn comprises a piston 4 movable in this cylinder and a piston drive 5 which engages on the piston. In addition, this device 1 may comprise a pulse generator 6, which—to effect the dispensing of samples from a liquid—is implemented to generate pressure waves in this liquid. An endpiece and/or a tip 8 is connected with the cylindrical chamber 3 via a line 7. This tip 8 is shown as a steel needle which attaches directly to the body and/or on the cylinder block 3' of the pump 2. The tip 8 implemented as a steel needle preferably adjoins the cylindrical chamber 3 of the pump 2 without a transition, so that the pipette tip made of steel represents a continuous narrowing of the pump cylindrical chamber 3. This design prevents the occurrence of undesired eddies and allows the unimpeded expansion of the pressure waves triggered by the pulse generator 6 in the liquid to be pipetted.

The piston drive 5 may comprise a first drive 9 and a second drive 10 implemented as a pulse generator 6. This first drive 9 is preferably implemented as a rotary spindle drive and comprises a spindle 11 and a first plate 12 movable with this spindle. The second drive 10 comprises a second plate 13 which is connected via a pulse generator 6 with the first plate 12 and which engages on the piston 4.

The space defined by cylindrical chamber 3 and piston 4, line 7, and tip 8 is preferably filled with a coherent liquid column, so that the volume of a liquid sample dispensed is defined, for a given tip geometry, solely by the parameters of a single pulse generated by the pulse generator 6. The cylindrical chamber 3 preferably contains 5 to 200 µl and the pulse generator 6 is implemented in this case as a preloaded stack of piezoelectric elements 14. Additional results show that pipetting can also be done with an air bubble and/or an "air gap" in the line 7.

Notwithstanding the illustration in FIG. 1, the tip 8 for pipetting of liquids can be implemented as a needle made of other materials or as a disposable tip made of plastic. Generally, the transition from the cylindrical chamber 3 to the tip 8 is then preferably produced with a so-called tip adapter 8'. Such a tip adapter is preferably produced from stainless-steel and is molded and outfitted in such a way that a secure and tight seat for a needle or disposable tip, produced, for example, from plastic, is ensured. The use of an O-ring between tip adapter 8' and tip 8 can favorably reinforce this seat and the required impermeability.

The specific arrangement of pump 2, piston drive 5, optional pulse generator 6, and tip 8 allows an extremely slender construction of the device 1, so that it is especially suitable for forming a component in a system for aspirating and dispensing liquid samples which comprises multiple devices 1 of this type. Such a system is, for example, a pipettor and/or (in the case of a system for dispensing samples) a dispenser. Such a system is preferably used for dispensing liquid into the wells of standard microplates with, for example, 96 wells (dispensing) or for aspirating liquids from one microplate and dispensing the samples in another microplate (pipetting). The reduction of the sample volumes (e.g. for filling high-density microplates having 384, 864, 1536, or even more wells) plays an increasingly important role, with the precision of the sample volume dispensed being assigned great importance. The time used for the dispensing and/or transferring of samples in these many wells is also significant. It is clear that multiple pipette tips which can be operated in parallel reduce the time used for the effective sample dispensing and/or for transferring by the same factor.

In principle, the consideration thus applies that a system having n devices, or at least such a system having n pumps 2, n lines 7, and n tips 8, having a first drive 9 and a second drive 10 and optionally having m pulse generators only needs 1/n of the dispensing time of a single device equipped with one of each of these components. The time factor thus plays a significant role during the filling of high-density microplates. These considerations are particularly significant if n is a multiple of 4—particularly 8, 96, or 384—and m is a whole number—particularly 1, 2, or 3.

Because the arrangement of the wells in the microplates corresponds to a two-dimensional array, the components of a system such as pump 2, piston drive 5, pulse generator 6, and tip 8 are preferably arranged in the same way. In order to achieve compact construction, the pumps 2 and tips 8 are arranged parallel to one another at the same time. An example of such an arrangement is shown in FIG. 2.

The need for rapid pipettors in the life science fields has driven the development of multichannel pipettors. In the known solutions, both the number of the channels and/or the tips and the ranges of the sample volumes to be pipetted vary. Approximately 1 µl can be assumed as the practical volume limit for free dispensing from the air in this case.

Figure 2:
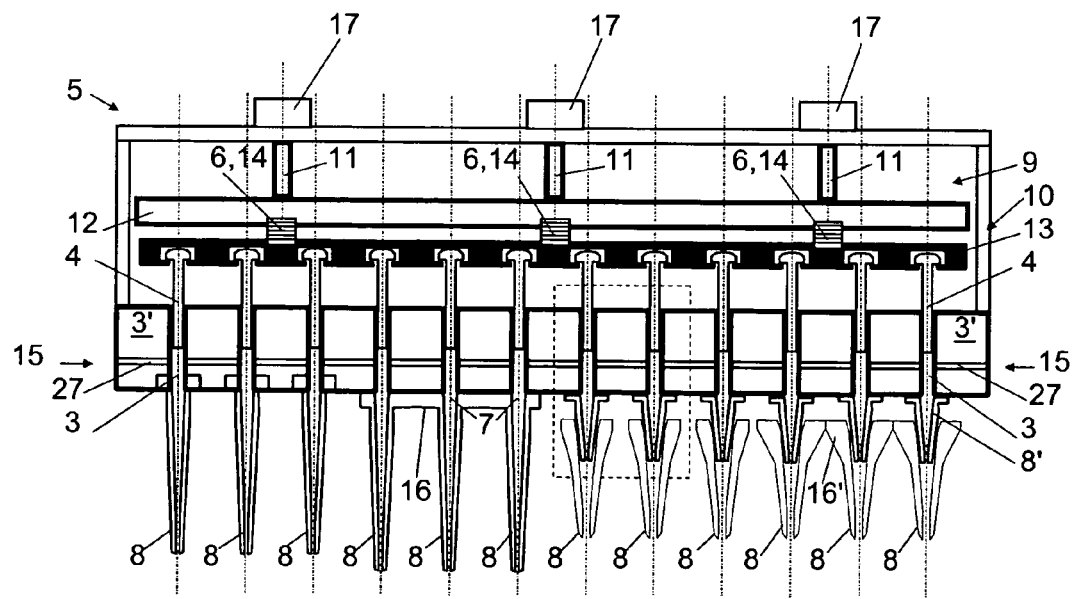
FIG. 2 shows a vertical section through a system for aspirating and dispensing liquid samples with an array of pumps and endpieces and/or tips arranged parallel to one another.

FIG. 2 shows a vertical section through a system for aspirating and dispensing liquid samples having an array of pumps 2 and tips 8 arranged parallel to one another. The example shown symbolizes an array of 12×8, i.e. 96, pumps 2 and tips 8. This array corresponds to the format and layout of a microplate with 96 wells. Each component of this system comprises a device 1 for aspirating and dispensing liquid samples having a pump 2, which comprises a cylindrical chamber 3, a piston 4 movable in this cylinder, and a piston drive 5 engaging on the piston, having a pulse generator 6, which—to effect the dispensing of samples from a liquid—is implemented for generating pressure waves in this liquid, and having a tip 8 connected via a line 7 with the cylindrical chamber 3, with the piston drive 5 comprising a first drive 9 and a second drive 10 implemented as a pulse generator 6. Each cylindrical chamber 3 preferably contains 5 to 200 µl, with the exact range depending on the layout, which can be conceived according to the planned use. These devices are characterized in that they comprise a channel 27 for flushing or rinsing the cylindrical chamber 3, with the channel 27 discharging into the cylindrical chamber 3. One such drive 9, 10 can be provided per pipetting channel, but individual parts of the drive 9, 10 can be simplified or combined in subassemblies.

The entire matrix of the 96 pistons 4 is moved by three spindles 11. In this case, these three spindles act on the first plate 12 and, via the three piezoelectric stacks 14, on the second plate 13, which in turn acts on the pistons 4 in the cylinders. The spindles 11 are each driven by one precision motor 17, so that a first drive 9 comprises three simultaneously rotating spindles 11, which act on a joint first plate 12. The first drive 9 serves for moving the pistons 4 during aspiration of liquids and for supplying liquid in the tips 8 during and/or after the dispensing of liquid samples from the tips.

The second drive 10 comprises, in this case, three pulse generators 6, each having a preloaded stack of piezoelectric elements 14, which connect the first plate 12 with the second plate 13. The two plates 12, 13 are preferably permanently connected with one another via the piezoelectric stacks in such a way that they can be moved toward and away from one another without oscillation by these piezoelectric actuators. An actuation of the piezoelectric stacks moves the second plate 13, and thus also the pistons 4, preferably by up to 20 µm. The second plate 13 simultaneously engages on all 96 pistons 4. For this purpose, the second plate 13 has recesses 18 in which the free ends 19 of the pistons 4 engage and/or in which these ends 19 are held. The 96 pistons 4 are components of an array of 96 pumps arranged in parallel to one another. The cylinders are implemented as borings 21 in a cylinder block 3', in each of which one piston 4 is movably arranged. 96 lines 7 and/or 96 tips 8 are connected to the cylinder chambers 3.

The endpieces and/or tips 8 can be implemented singly, i.e. individually for each channel (as described under FIG. 1) or as tip plates 16, 16' having a corresponding number of, in this case, 96 tips 8. In FIG. 2, four examples (from left to right) of tips 8 are shown, in this case the first three are shown as single steel tips 8, the second three as a steel tip plate 16, the third three as single disposable tips 8, and the fourth three as a disposable tip plate 16'. Preferably, seals (not shown) are located between each of the tips 8 and their adapters 8' so that a secure seating of the tips 8 on their respective adapter 8' and/or the impermeability of the line 7 between piston 4 and pipette tip 8 is guaranteed.

Figure 3:
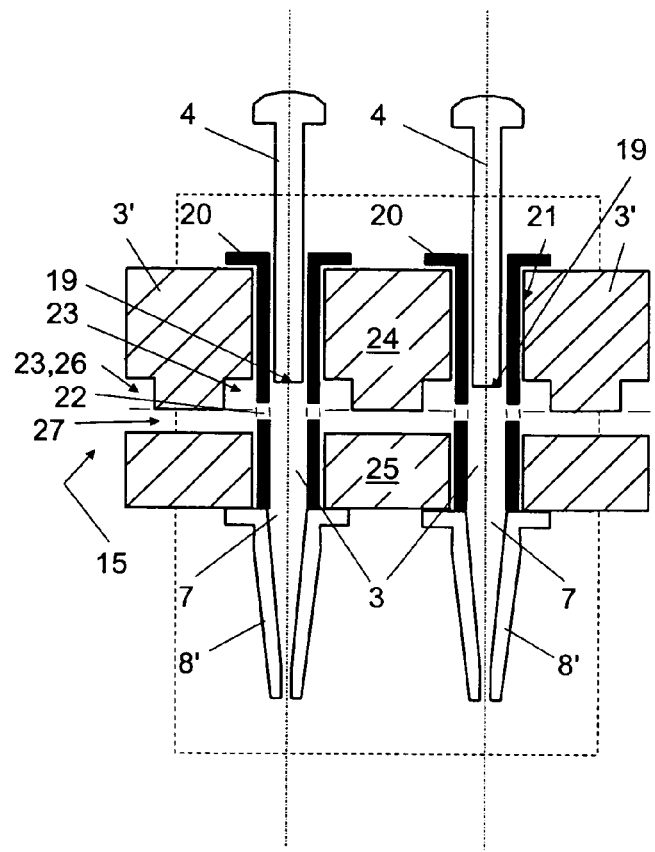
FIG. 3 shows an enlarged detail from FIG. 2, corresponding to the field indicated there.

In order that air bubbles can be prevented in or removed from the liquid which fills the pipetting or dispensing channels, i.e., the cylindrical chambers 3, the lines 7, and the tips 8, a channel system 15 is provided for rinsing or flushing the cylindrical chambers 3 in the cylinder block 3'. Via a line (31, see FIG. 6), the entire channel system 15 and all cylindrical chambers 3 can thus be filled with liquid from the rear (not through the pipette tips 8) and thus be rinsed or flushed. The discharge of this channel system 15 in the region of the cylindrical chambers 3 is also illustrated in FIG. 3. The cylindrical chambers 3 are identical in this exemplary embodiment with the inside of sleeves 20 which are inserted in borings 21 of the cylinder block 3'. Alternatively, the borings 21 in the cylinder block 3' can be used directly as cylinders (cf. FIG. 2 and FIG. 6). Alternatively to the channel system 15 having single channels 27 shown in FIG. 3, the supply of the pumps 2 can occur via a simpler channel system 15 (cf. FIG. 2 and FIG. 6). This extends essentially over the entire surface of the plates 12, 13 at approximately the same height and represents a simple, coherent cavity (27').

If sleeves 20 are used, these have a lateral, particularly continuous opening 22, which communicates with the channel system 15. In order that the individual rotational position of the sleeves 20 does not have any influence on the connection by the channel system 15, the channel system has an enlargement 23 in the region of each sleeve 20. In this case, the cylinder block 3' is preferably produced in two parts. In this case, circular depressions 26 are located in a first part 24 of the cylinder block 3' and the single channels 27 of the channel system 15 are located in a second part 25 of the cylinder block 3'. This can—depending on the material (glass, steel, plastic etc.), which is selected for the parts of the cylinder block 3'—be performed with embedding, milling, etching, or other suitable methods. An injection molded part 24, 25 made of plastic can also have such channels 27.

Alternatively to this embodiment, depressions 26 and single channels 27 can also be molded into one part of the cylinder block 3' and the other part of the cylinder block 3' can be implemented as a plate. Notwithstanding the illustration in FIG. 3, the lower end of the sleeves 20 can be directly implemented as a tip adapter 8'. In addition, the actuation, i.e. the pressure wave generation, deviating from the use of one or more piezoelectric stacks, can be produced, for example, by a pneumatic, magnetic, or thermal pulse generator. As another alternative to the embodiment shown, the first and/or the second plate (12, 13) can have a shape deviating from a rectangle and, for example, have a square, hexagonal, octagonal, oval, or even round shape.

Optionally, a pulse is output from the pulse generator 6 implemented as a piezoelectric stack 14 onto the second plate 13. This plate 13 relays the impact to the individual pistons 4, which perform a correspondingly short and targeted movement in their cylindrical chambers 3. This movement triggers a pressure wave in the liquid in each cylindrical chamber 3 simultaneously. The position of the pistons 4 within the cylindrical chamber 3 is preferably selected for this triggering of pressure waves (deviating from the illustration in FIG. 3) in such a way that the free piston ends 19 come to rest between the openings 22 and the line 7. In this way, the openings 22 are sealed by the pistons 4 and the pressure waves can expand in the liquid only to the pipette tips 8, as desired. The openings 22 preferably have as large an area as possible and the single channels 27 have a large inner diameter, in order that the wash or flush liquid experiences the least possible flow resistance.

Deviating from these illustrations in FIGS. 2 and 3, for example, 4 or 8 and/or even 16 or more pumps 2 and tips 8 can be arranged in a linear array which is made up of one single row. Preferably, however, 96, 384, or more pumps 2 and tips 8 are arranged in parallel in a two-dimensional array in such a way that this array corresponds to the format and the layout of a microplate with 96, 384, 864, 1536, or more wells. Such an array of pumps 2 and tips 8, each arranged parallel to one another, allows the simultaneous aspiration or dispensing of 96, 384, or more samples, which allows the time for processing of a corresponding high-density microplate to be significantly reduced.

Figure 4:
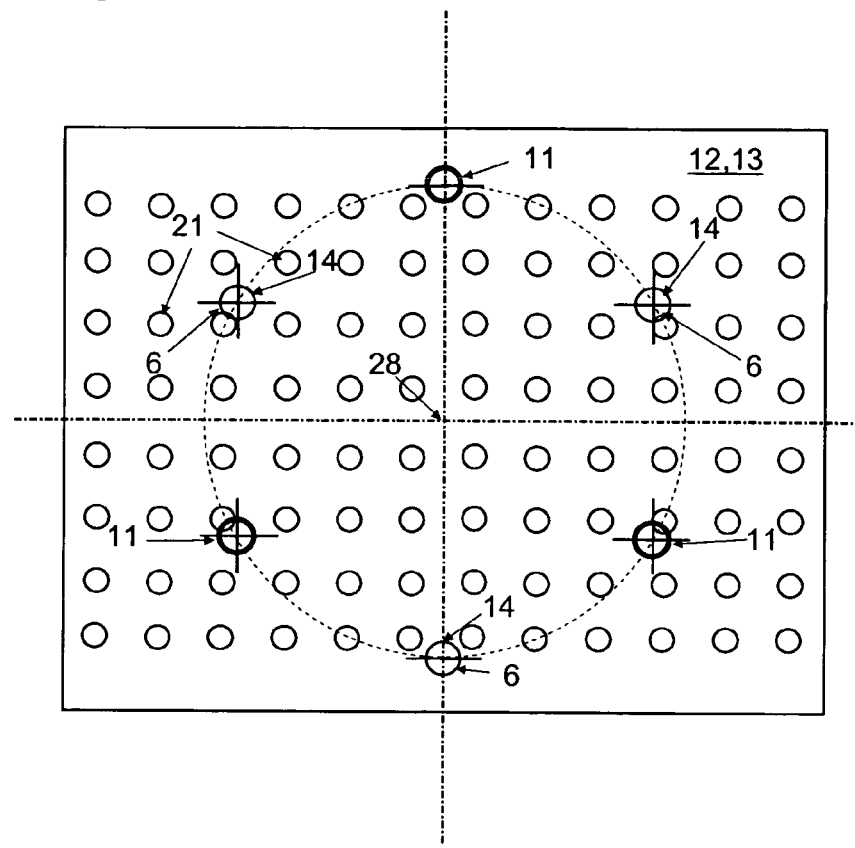
FIG. 4 shows a horizontal projection of a layout of the piston drive according to a first embodiment.

FIG. 4 shows, in a horizontal projection, a layout of the piston drive 5 according to a first embodiment. Three spindles 11 and three pulse generators 6 are each positioned at the same distance from the center of the cylinder block 3' and/or the two plates 12, 13, with this same distance also lying between them and the nearest pulse generator 6 and/or spindle 11. A trigonal symmetry whose center 28 lies in the center of the cylinder block 3' and/or the two plates 12, 13 results from this. This symmetry allows uniform distribution of the forces in the plates 12, 13 and thus uniform displacement of the plates with the first drive 9 and the second drive 10. In this case as well, the liquid is fed into the tip with the first drive, so that before each pulse by the second drive, a coherent liquid column fills up the active space of cylindrical space 3, line 7, and tip 8. The layout described has the advantage that the levels of the plates 12, 13 are never redundant and that only three piezoelectric stacks are sufficient to dispense 96 or even 384 or more samples simultaneously.

Figure 5:
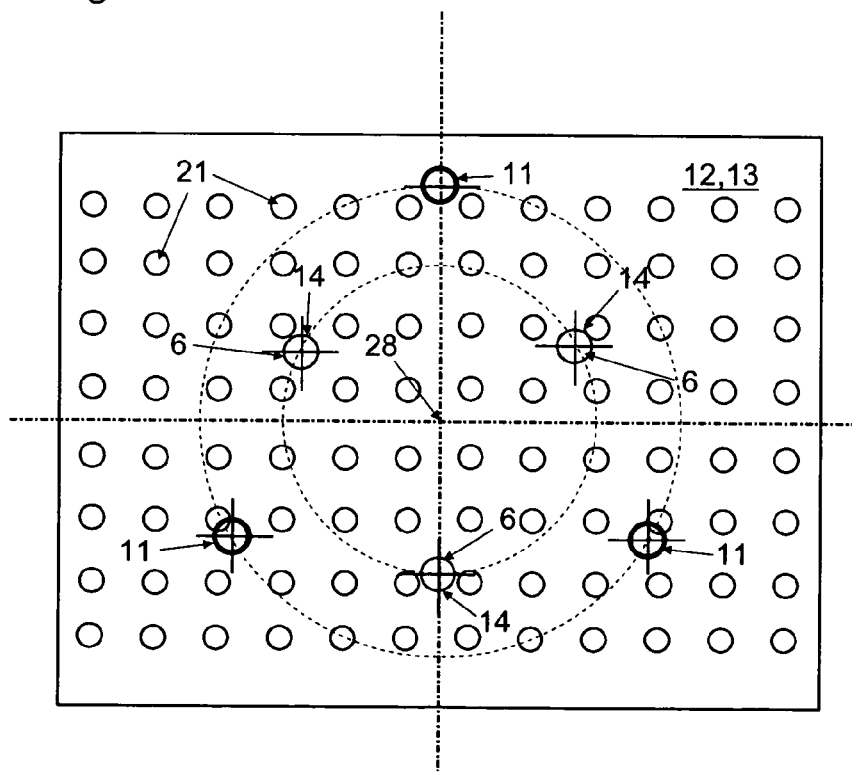
FIG. 5 shows a horizontal projection of a layout of the piston drive according to a second embodiment.

FIG. 5 shows a horizontal projection of a layout of the piston drive according to a second embodiment. In contrast to FIG. 4, in this case the spindles 11 and the pulse generators 6 are not located on a common graduated circle (indicated with dashed lines). However, the spindles 11 and/or the pulse generators 6 each define a triangle, whose center of gravity always corresponds with the center of symmetry 28, in both FIG. 4 and in FIG. 5. The symmetry achieved in this way allows uniform distribution of the forces in the plates 12, 13 and therefore uniform displacement of these plates with the first drive 9 and the second drive 10. Further arrangements which correspond to this symmetry principle are included in the extent of this invention.

Figure 6:
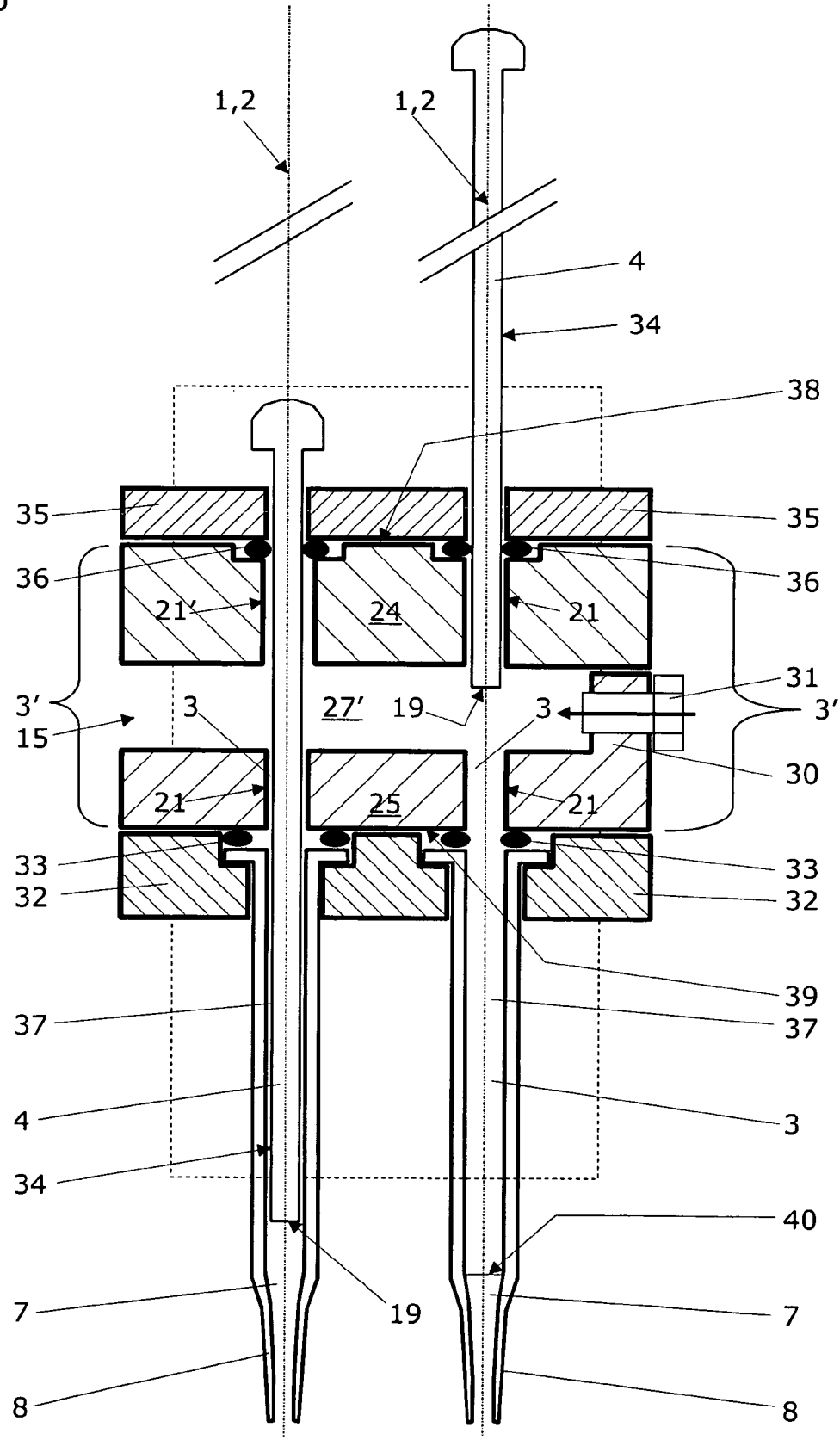
FIG. 6 shows an enlarged detail from FIG. 2, corresponding to the field indicated there and according to an especially preferred embodiment.

FIG. 6 shows an enlarged detail from FIG. 2, corresponding to the field indicated there and according to an especially preferred embodiment. This embodiment preferably comprises borings 21 in the cylinder block 3', which are used as cylinders 3 (cf. FIG. 2) or in which sleeves 20 are introduced that form the cylinders 3 (cf. FIG. 2). The channel system 15 for supplying the pumps 2 with a flushing or rinsing fluid—instead of having single channels 27 as shown in FIG. 3—is a simpler channel system 15, which extends essentially over the entire surface of the plates 12, 13 (see FIG. 2) at approximately the same height, and which represents a simple, coherent cavity 27'. In this especially preferred embodiment, the coherent cavity 27' is molded into one part of the cylinder block 3' and the other part of the cylinder block 3' is implemented as a plate. It goes without saying that the coherent cavity 27' in the part of the cylinder block 3' can be closed by plate-like part of the block 3' as a superimposed cover (see FIG. 6) or as an undenying base (not illustrated).

On the circumference of the coherent cavity 27', there is located a wall 30 or a similar barrier in order to close the coherent cavity 27'. Preferably, this circumferential barrier is implemented as a wall 30 that is attached or molded to a second or lower part 25 of the cylinder block 3'. Alternatively, the coherent cavity 27' can be machined or molded into the second part 25. It goes without saying that the parts 24 and 25 can be exchanged in function and/or position according to the actual requirements. Preferably in this wall 30, at least one feed through 31 is situated for attachment of a line that feeds flushing or rinsing fluid to the coherent cavity 27' (see arrow in FIG. 6). As outlet for these flushing or rinsing fluids, the pipette tips 8 or another feed through 31' (not shown) can be utilized. Preferably, seals 33 (shown in FIG. 6) are located at each of the tips 8 so that the impermeability between the pipette tip 8 and the surrounding air is guaranteed (see both pistons in FIG. 6).

The position of the pistons 4 within the cylindrical chambers 3 is preferably selected for aspiration or dispensing of samples in such a way that the free piston ends 19 come to rest between the coherent cavity 27' and the line 7. In accordance to this, FIG. 6 illustrates a system with a plurality of devices 1 for aspirating and dispensing liquid samples. Each one of these devices 1 comprises a pump 2 that comprises a cylindrical chamber 3 located in a cylinder block 3', a piston 4 movable in this cylindrical chamber and a piston drive 5 (see FIG. 1) that engages the piston. The device further comprises a tip 8 with a line 7. The cylindrical chamber 3 is connected to a channel system 15 for flushing or rinsing the cylindrical chamber 3, into which it discharges. The cylinder block 3' preferably comprises two parts 24,25 that are separated by and enclosing an intermediate channel system 15, wherein the cylindrical chamber 3 entirely penetrates the lower part 25 of the cylinder block 3'. The piston 4 entirely seals this cylindrical chamber 3 from the channel system 15 or the coherent cavity 27' respectively, if the piston 4 is positioned in the cylindrical chamber 3 in such a way that the free piston end 19 comes to rest between the channel system 15 and the line 7. With the piston 4 in this position (see left side of FIG. 6), the entire cylindrical chamber 3, which at least reaches from the coherent cavity 27' to the bottom 39 of the cylinder block 3' or deep into the tip 8, is sealed and separated from the channel system 15, i.e., from the coherent cavity 27'. In variants to this embodiment, the diameter of the boring 21' in the part 24 at the top 38 of the cylinder block 3' can be wider than the diameter of the boring 21 in the cylinder block part 25 (see left side of FIG. 6) or the boring 21 can be of the same diameter in both parts 24,25 (see right side of FIG. 6). In all variants, the boring 21 or 21' in the first or upper part 24 of the cylinder block 3' is not part of the cylindrical chamber 3 and does not contribute to the aspiration or the dispense of liquids.

According to a first embodiment, the cylindrical chamber 3 is implemented as a sleeve 20 that is inserted in a boring 21 located in a cylinder block 3'. In this case, the sleeve 20 preferably has at least one opening 22 that communicates with the channel system 15 (see FIG. 3). The sleeve 20 preferably reaches through the entire cylinder block 3' (see FIG. 3). The channel system 15 discharges into the cylindrical chamber 3 with these openings 22, which are sealed by the piston 4, if the piston 4 is positioned in the cylindrical chamber 3 in such a way that a free piston end 19 comes to rest between the openings 22 and the line 7. Preferably, the cylinder block 3' comprises a first or upper part 24 implemented as a plate and a second or lower part 25 comprising the channel system 15 that is implemented as a channel 27 or coherent cavity 27' for flushing or rinsing the cylindrical chamber 3.

According to a preferred, second embodiment, the cylindrical chamber 3 is implemented as a boring 21 located in a cylinder block 3'. In this case, the cylinder block 3' comprises a first part 24 implemented as a plate and a second part 25 comprising the channel system 15 that is implemented as a channel 27 or coherent cavity 27' for flushing or rinsing the cylindrical chamber 3 (see FIG. 6). The cylindrical chamber 3 preferably reaches through the entire part 25 of the cylinder block 3' (see FIGS. 2 and 6). Preferably, the channel system 15 is a coherent cavity 27' located in the second part 25 of the cylinder block 3', which coherent cavity 27' is covered by the plate-like first part 24 of the block 3' and sealed around its circumference. These two parts 24,25 can be welded, glued, or simply pressed together in order to seal the circumference of the coherent cavity 27'. Optionally, an O-ring seal is placed between the two parts 24,25, one or both of them comprising an sealing flange (not shown) and/or a sealing wall 30.

It is further preferred that the piston drive 5 comprises a first drive 9 with a first plate 12, which first plate 12 is connected with a second plate 13 that engages on the piston 4 (see FIGS. 1 and 2). It is also preferred that the line 7 defines a volume with a conical shape that extends below this cylindrical chamber 3 and this second part 25 of the cylinder block 3' (see also FIGS. 1-3). In this especially preferred embodiment, the piston drive 5 preferably comprises a first drive 9 with a first plate 12, which first plate 12 is connected with a second plate 13 that engages on the piston 4. According to an additional alternative embodiment, first and second plates 12,13 can be combined in a single connection plate that is made from one single piece or of two pieces and that connects the first piston drive with the pistons 4 (not shown).

As noted, it is especially preferred that the cylindrical chamber 3 at least entirely penetrates the second part 25 of the cylinder block 3', and that the line 7 defines a volume with a conical shape that extends below this cylindrical chamber 3 and this second part 25 of the cylinder block 3' (see FIGS. 2 and 6). In this case, the piston 4 entirely seals and separates the cylindrical chamber 3 from the coherent cavity 27' as soon as the free end 19 of the piston 4 is moved close to the bottom 39 of the cylinder block 3'. The cylindrical chamber 3 is implemented as a boring 21 and extends into a cylindrical part 37 of a pipette tip 8. This cylindrical part 37 of the pipette tip 8 may reach to a lower limit 40 that is located close to the line 7. This cylindrical part 37 of the pipette tip 8 may have a larger diameter than the cylindrical chamber 3 inside of the cylinder block 3'. In this case, the conical line 7 situated inside this tip 8 is spaced apart from the second part 25 of the cylinder block 3' by said cylindrical part 37, such that the free end 19 of the piston 4 is movable beyond the cylindrical chamber 3 and into the cylindrical part 37 of the tip 8. When doing this, the piston 4 is controllably reducing the volume inside a pipette tip 8, which results in accurate pipetting capability.

It is further preferred that the pipette tip 8 is sealably connected to the second part 25 of the cylinder block 3' by a connector plate 32. In this case, an O-ring seal 33 is squeezed between the tip 8 and the second part 25 of the cylinder block 3'. This squeezed O-ring seal 33 ensures that no air or liquid can escape from or enter into the pipette tip 8 other than through the coherent cavity 27' or the orifice of the pipette tip 8.

It is recalled here that the coherent cavity 27' is separated and sealed from the entire cylindrical chamber 3 and also from the orifice pipette tip 8 as soon as the free end 19 of the piston 4 is moved at least close the bottom 39 of the cylinder block 3'. It is preferred that system liquid, which is utilized for flushing or rinsing the cylindrical chambers 3 and the pipette tips 8 from behind, preferably fills the coherent cavity completely. Preferably, this system liquid is kept at ambient pressure during pipetting (see left side of FIG. 6). The space between the piston 4 and the wall of the cylindrical chamber 3 measures from 50 to 150 μm, preferably 100 μm. The space between the piston 4 and the wall of the pipette tip 8 preferably is smaller than 100 μm. This space more preferably is smaller than 50 μm, and most preferably measures about 25 μm. Typically, the diameter of the piston is 1.25 mm. Thus, system liquid may enter into this small space by capillary forces and—through wetting the outer surface 34 of the piston 4 as well as the wall of the cylindrical chamber 3 or the wall of the pipette tip 8—the system liquid acts as a seal between the orifice of a pipette tip 8 and the coherent cavity 27'. Another connector plate 35 presses an O-ring seal 36 against the first part 24 of the cylinder block 3'. This squeezed O-ring seal 36 is sealably pressed onto an outer surface 34 of the piston 4 of the pump 2 (see both pistons in FIG. 6). This O-ring 36 prevents system liquid from escaping from the coherent cavity 27' when the system liquid is pressurized.

In a first alternative embodiment (not shown), the space between the piston 4 and the wall of the pipette tip 8 is larger than the space between the piston 4 and the wall of the cylindrical chamber 3. In this case sealing and separation of the pipette orifice from the coherent cavity 27' occurs again when the free end 19 of the piston 4 is moved at least close the bottom 39 of the cylinder block 3'. Also in this case, the piston 4 is controllably reducing the volume inside a pipette tip 8, which results in accurate pipetting capability.

In a second alternative embodiment, which could be combined with the first alternative embodiment (see right side of FIG. 6), the O-ring 33 is also sealably pressed onto the outer surface 34 of the piston 4 of the pump 2. The lower O-ring seal 33 then enhances the sealing capability of the piston 4 during pressurizing the system liquid inside of coherent cavity 27'.

The device according to the alternative embodiment of the present invention provides for a system for aspirating and dispensing liquid samples. This system preferably comprises a plurality of such devices 1. In this case, the devices 1 are arranged in an array of pumps 2 and tips 8 that are arranged in parallel to one another. It is especially preferred that this array corresponds in layout and format to a microplate having 96, 384, 864, 1536, or more wells. In such preferred systems, the tips 8 are implemented as single tips 8 or tip plates 16, 16' that can be removed or automatically picked up and discarded. For automated working, the system further comprises a computer for controlling the aspiration and dispensing of liquid samples.

For pipetting from, for example, a 96 well microplate, if disposable tips are used, first these are picked up. The plates 12, 13 are pulled back with the first drive 9 far enough that the ends 19 of the pistons 4 come to rest behind the openings 22 in the sleeves 20. The channels 27, the cylindrical chambers 3, the lines 7, and/or the tips 8 and tip adapters 8' are then rinsed or flushed and/or filled with system liquid (e.g. with deionized or distilled water). Subsequently, the pistons 4 are moved in the direction of the tips 8 in order to prepare the pumps 2 to aspirate liquid via the tips. If the pistons 4 are moved to their forwardmost position in this case, a maximum aspiration capacity is made available. After the array having 96 pumps 2 and tips 8 is moved over the liquid to be aspirated, the tips are dipped somewhat into the liquid. By pulling back the pistons 4 with the first drive 9, with the path being determined by the rotation of the spindles 11, the aspiration of the liquid to be pipetted occurs, and does so simultaneously in all tips 8.

Corresponding components have the same reference numbers in the figures.

Flushing or rinsing of a single device 1 or of a system comprising a plurality of such devices 1 is now described in more detail for the utilization of devices according to the second embodiment with the cylindrical chamber 3 implemented as a boring 21 located in a cylinder block 3'. Such flushing or rinsing preferably is carried out according to the following procedural steps:

1. All pistons 4 are moved into a Ø-position. In this position, the free ends 19 of the pistons 4 are closest to the openings of the tips 8. This extreme position is assumed in order to displace excess volume air gaps and liquid from the tips 8. With the pistons 4 in this position, the channel system 15, or the coherent cavity 27' respectively, is separated entirely from all cylindrical chambers 3 and thus, the pipette tip orifices; no matter how wide the inner diameter of the pipette tip may be.
2. Flushing or rinsing of the coherent cavity 27' is carried out by introducing a flushing or rinsing fluid, such as a system liquid (e.g. deionized or distilled water) through inlet 31. Draining occurs through an appropriate outlet via an outlet valve (both not shown) that preferably are situated on an opposite side of the coherent cavity 27'. The liquid preferably is introduced with a pressure of 1.4 bar; more preferably with a pressure oscillating between 1.0 and 1.4 bar at an opening and closing frequency of an inlet valve (not shown) in the order of 1 Hz. Pulsed flushing enhances the chances to remove all air bubbles in the coherent cavity 27'. The outlet valve is continuously held open during flushing or rinsing.
3. After closing the outlet valve, all free ends 19 of the pistons 4 are moved away from the openings of the tips 8. During this preferably vertical up movement of the pistons 4, the inlet valve is open and a preferred overpressure of 1.4 bar is established in the coherent cavity 27'. As soon as the pistons 4 do not separate the coherent cavity 27', from the cylindrical chambers 3 any more, system liquid (e.g. deionized or distilled water) is driven out through the cylindrical chambers 3, the tips 8, and the openings of the latter.
4. Still keeping the inlet valve open and the outlet valve closed, all free ends 19 of the pistons 4 are moved again into the O-position. With the pistons 4 in this position, the channel system 15, or the coherent cavity 27' again is separated completely from all cylindrical chambers 3.
5. The inlet valve is closed and the outlet valve is opened to release excess pressure from the coherent cavity 27'. The system is now ready for the aspiration of liquid samples.

For dispensing, the pistons 4 are moved toward the tips 8. In order for the liquid to break away cleanly from the tips 8 and therefore to produce exact volumes, a specific minimum speed and abrupt stopping of the pistons 4 at the end of dispensing is necessary. For volumes to be dispensed which are in the microliter range, the first drive 9 is typically sufficient for precise sample dispensing. In the sub-microliter range, in contrast, acceleration and abrupt stopping of the spindle drive is no longer sufficient to ensure that the liquid to be dispensed breaks away cleanly. For this reason, the pistons 4 are additionally moved with an optional second drive 10 by piezoelectric actuation.

This actuation occurs through appropriate electrical rectangular pulses output with a frequency of 1 to 1000 Hz at the piezoelectric stacks 14, which are performed simultaneously with the movement of the piston matrix and, together with this movement, determine the volume of the samples to be dispensed. These movements of the two drives 9, 10 are preferably synchronized in such a way that the first pulse occurs with the beginning of the travel of the pistons 4 and the last pulse with the end of this travel. Due to this synchronization, the piezoelectric actuation ensures that the droplets break away cleanly, even if the piston matrix moves slowly. This is made possible, as described, by transmission of the pulses triggered by the pulse generator 6 and transferred with the second plate 13 onto the pistons 4 and thus onto the liquid in the cylindrical chambers 3.

For dispensing in the range of a few nl, the single droplet volume can also be determined solely by the strength of the piezoelectric actuation. The total volume dispensed is thus a product of the number of droplets and their content. The single droplet size is determined in this type of dispensing primarily by the strength of actuation and by the diameter of the opening of the pipette tip 8. These two parameters are then also preferably adjusted to the quantity and the physicochemical properties of the liquid to be pipetted.

Four operating modes result from the aforementioned:

A Large Volumes

The dispensing of volumes of more than one microliter is performed by advancing the pistons 4 and is determined solely by the first drive 9, implemented as a spindle drive.

B Medium Volumes

The dispensing of droplets between 0.5 and 1 µl is performed by advancing the pistons 4 and is determined by the first drive 9, implemented as a spindle drive. The additional piezoelectric actuation allows the droplets to break away cleanly. Furthermore, the following variants are possible:

B1 After the piston 4 is advanced, the piezoelectric stack is actuated once in order to ensure clean droplet breakaway from the air.

B2 Before the piston 4 is displaced, the piezoelectric stack is actuated once in order to generate a defined breakaway edge in the tip. The volume is defined by the advance of the piston 4 and the piezoelectric actuation allows droplet breakaway at the same position.

B3 The piezoelectric actuator is activated during the entire advance of the piston 4 and the liquid stream is "chopped" into single droplets. The volume is defined by the advance.

C Small Volumes

The dispensing of droplets of less than 0.5 µl is performed by the second drive 10, implemented as a piezoelectric actuator. The advancing of the pistons 4 with the first drive 9, implemented as a spindle drive, serves for compensating for the volumes dispensed. Ideally, the compensation occurs in such a way that the space defined by cylindrical chamber 3, piston 4, line 7, and tip 8 is completely filled with a coherent liquid column at least before the next pulse output. Therefore, when the system according to the invention is used, the volume of a liquid sample dispensed is defined, for a given tip geometry, solely by the parameters of one single pulse generated by the pulse generator 6.

D Very Small Volumes

If the liquid column is pulled back slightly from the tip opening, it becomes possible to eject single droplets of up to 10 nl out of a tip opening of up to 500 µm in diameter with single pulses of the piezoelectric actuator. The droplet volume is therefore only dependent on the pulse strength, but not on the diameter of the opening.

All of the pipetting modes described above can be used both with or without an air bubble ("separation air gap") for separating samples and system liquid. Also, both fixed tips and disposable plastic tips can be used. Without the separation air gap, pipetting can be performed somewhat more precisely than with an air gap, but the sample is somewhat diluted by the system liquid, which causes somewhat more sample material to be aspirated than is dispensed. The slightly diluted residue is discarded.

A great advantage of the devices and systems according to the invention is that, with one single device, large, medium, and small sample volumes can be dispensed with high precision and with practically any desired number of channels (single pipettes up to arrays with 384 and more pipettes).

The diameter of the opening of the pipette tip 8 is, depending on the volume range desired of the samples to be dispensed, 25 µm to 500 µm. The inner diameter of the pipette tips and/or the needles tapers from approximately 0.5 mm to 1 mm toward the outlet of the tip 8. The faces of the tips 8 are to be as small as possible within the framework of production capabilities.

The devices 1 and systems according to the invention preferably comprise a computer—e.g. integrated or also provided—for synchronizing the two drives 9, 10 and/or for controlling the aspiration and dispensing of liquid samples.

What is claimed is:

1. A device for aspirating and dispensing or for dispensing liquid samples comprising:
   at least one piston pump that in each case comprises a cylinder block with a cylindrical chamber having a wall, a pump piston comprising a free piston end and being movable in said cylindrical chamber, and a pump piston drive that engages the piston;
   at least one pipette or dispenser tip connected to the cylindrical chamber with a line in each case, and
   a channel or channel system that discharges into the cylindrical chamber(s) for flushing or rinsing the cylindrical chamber(s),
   wherein the cylinder block comprises a first part and a second part, between which first and second cylinder block parts the channel or channel system is located, wherein the first and second block parts comprise respective first and second seals, the first and second seals touching the outer surface of the pump piston for sealing the channel or channel system against the environment, wherein the free end of each pump piston is capable of being positioned between the first seal and the channel or channel system for flushing or rinsing the cylindrical chamber and is capable of being positioned between the channel or channel system and the line for aspirating or for dispensing liquid samples, and wherein the second seal entirely seals the cylindrical chamber from the channel or channel system during aspirating or dispensing liquid samples, while the free end of the pump piston is positioned between the channel or channel system and the line such that the second seal touches the outer surface of the pump piston.

2. The device of claim 1, wherein the piston drive comprises a first drive with a first plate that is connected with a second plate, which engages on the piston.

3. The device of claim 1, wherein the cylindrical chamber is implemented as a sleeve that is inserted in a boring, which is located in a cylinder block.

4. The device of claim 1, wherein the cylindrical chamber is implemented as a boring that is located in a cylinder block.

5. The device of claim 4, wherein the cylindrical chamber entirely penetrates a second, lower part of the cylinder block.

6. The device of claim 4, wherein a first part of the cylinder block is implemented as a plate and a second part of the cylinder block comprises the channel system, which is implemented as a coherent cavity.

7. The device of claim 4, wherein the channel system is a coherent cavity that is located in a second part of the cylinder block, which coherent cavity is covered by a plate-like first part of the cylinder block and which coherent cavity is sealed around its circumference.

8. The device of claim 4, wherein the line defines a volume with a conical shape that extends below this cylindrical chamber and a second, lower part of the cylinder block.

9. The device of claim 8, wherein the cylindrical chamber extends into a cylindrical part of the at least one pipette or dispenser tip, the conical line situated inside this at least one pipette or dispenser tip being spaced apart from the second part of the cylinder block by said cylindrical part, such that the free end of the piston is movable beyond the cylindrical chamber and into the cylindrical part of the at least one pipette or dispenser tip.

10. The device of claim 9, wherein the at least one pipette or dispenser tip is sealably connected to the second part of the cylinder block by a connector plate, and wherein the second seal is an O-ring seal which is squeezed between the at least one pipette or dispenser tip and the second part of the cylinder block.

11. The device of claim 1, wherein each of said first and second seals is selected from the group consisting of a fluid seal, an o-ring seal, and combinations thereof.

12. A system for aspirating and dispensing liquid samples, which comprises a plurality of devices according to claim 1, the devices being arranged in an array of pumps and tips arranged in parallel to one another, wherein this array corresponds in layout and format to a microplate having 96, 384, 864, 1536, or more wells.

13. A system according to claim 12, wherein the tips are implemented as single tips or tip plates that can be removed or automatically picked up and discarded.

14. A system according to claim 12, further comprising a computer for controlling the aspiration and dispensing of liquid samples.

* * * * *